US010269096B2

United States Patent
Hancock

(10) Patent No.: US 10,269,096 B2
(45) Date of Patent: Apr. 23, 2019

(54) CLUTTER SUPPRESSION FOR SYNTHETIC APERTURE ULTRASOUND

(71) Applicant: Volcano Corporation, San Diego, CA (US)

(72) Inventor: Andrew Hancock, Sacramento, CA (US)

(73) Assignee: VOLCANO CORPORATION, San Diego, CA (US)

( * ) Notice: Subject to any disclaimer, the term of this patent is extended or adjusted under 35 U.S.C. 154(b) by 636 days.

(21) Appl. No.: 14/867,984

(22) Filed: Sep. 28, 2015

(65) Prior Publication Data

US 2016/0104267 A1 Apr. 14, 2016

Related U.S. Application Data

(60) Provisional application No. 62/062,698, filed on Oct. 10, 2014.

(51) Int. Cl.
*G06K 9/40* (2006.01)
*G06T 5/00* (2006.01)
(Continued)

(52) U.S. Cl.
CPC ............... *G06T 5/002* (2013.01); *A61B 8/12* (2013.01); *A61B 8/52* (2013.01); *A61B 8/5207* (2013.01);
(Continued)

(58) Field of Classification Search
CPC .. G06K 9/40; G06T 5/00; G06T 5/001; G06T 5/002; G06T 7/0012; G06T 2207/10132;
(Continued)

(56) References Cited

U.S. PATENT DOCUMENTS 5,910,115 A * 6/1999 Rigby ................. G01S 7/52026
600/443
6,071,240 A * 6/2000 Hall .................... G01S 7/52026
600/443
(Continued)

OTHER PUBLICATIONS

Jorge Camacho, Montserrat Parrilla, and Carlos Fritsch, "Phase Coherence Imaging", IEEE, Transactions on Ultrasound, Ferroelectrics, and Frequency Control, vol. 56, No. 5, May 2009, pp. 958-974.*

*Primary Examiner* — Eric Rush

(57) ABSTRACT

Solid-state ultrasound imaging devices, systems, and methods are provided. Some embodiments of the present disclosure are particularly directed to identifying and removing artifacts in ultrasound data due to side lobes, grating lobes, and/or other effect. In some embodiments, an ultrasound processing system includes an interface operable to receive A-line signal data and a focusing engine operable to perform a focusing process on the received A-line signal data to produce focused A-line signal data. The ultrasound processing system also includes a coherency unit operable to determine a measurement of coherency of the received A-line signal data. The ultrasound processing system further includes an adjustment unit operable to determine an adjustment to the focused A-line signal data based on the measurement of coherency, and a compensation unit operable to apply the adjustment to the focused A-line signal data.

25 Claims, 8 Drawing Sheets

(51) Int. Cl.
*A61B 8/08* (2006.01)
*G01S 7/52* (2006.01)
*A61B 8/12* (2006.01)
*G01S 15/89* (2006.01)

(52) U.S. Cl.
CPC .......... *A61B 8/5269* (2013.01); *A61B 8/5276* (2013.01); *G01S 7/52026* (2013.01); *G01S 7/52046* (2013.01); *G01S 7/52047* (2013.01); *G01S 7/52049* (2013.01); *G01S 7/52077* (2013.01); *G01S 15/8915* (2013.01); *G06K 9/40* (2013.01); *G06T 2207/10004* (2013.01); *G06T 2207/10132* (2013.01); *G06T 2207/30101* (2013.01)

(58) Field of Classification Search
CPC . G06T 2207/20182; G06T 2207/30004; G06T 2207/30101; G06T 2207/30168; G01S 7/52003; G01S 7/52026; G01S 7/52046; G01S 7/52047; G01S 7/52049; G01S 7/52077; G01S 15/8915; A61B 5/0066; A61B 8/00; A61B 8/12–8/14; A61B 8/145; A61B 8/15; A61B 8/52; A61B 8/5207; A61B 8/5269; A61B 8/58276; A61B 8/58
USPC ....... 382/128, 131, 132, 254, 255, 270–275; 278/4, 9, 11–15, 21; 128/916; 600/407, 600/437, 442–445, 447–450, 458, 459, 600/462, 466, 467
See application file for complete search history.

(56) References Cited

U.S. PATENT DOCUMENTS

| | | | |
|---|---|---|---|
| 7,846,101 B2 | 12/2010 | Eberle et al. | |
| 7,921,717 B2* | 4/2011 | Jackson | G03B 42/06 600/443 |
| 8,208,724 B2* | 6/2012 | Lankoande | G06K 9/0063 382/173 |
| 2004/0054282 A1* | 3/2004 | Aubry | A61B 8/15 600/437 |
| 2005/0228279 A1* | 10/2005 | Ustuner | G01S 15/8927 600/443 |
| 2006/0173313 A1* | 8/2006 | Liu | G01S 7/52046 600/437 |
| 2007/0239024 A1* | 10/2007 | Eberle | G10K 11/004 600/459 |
| 2012/0277589 A1* | 11/2012 | Katou | A61B 8/4405 600/443 |
| 2013/0109971 A1* | 5/2013 | Dahl | A61B 8/08 600/447 |

* cited by examiner

CLUTTER SUPPRESSION FOR SYNTHETIC APERTURE ULTRASOUND

CROSS REFERENCE TO RELATED APPLICATIONS

The present application claims priority to and the benefit of the U.S. Provisional Patent Application No. 62/062,698, filed Oct. 10, 2014, which is hereby incorporated by reference in its entirety.

TECHNICAL FIELD

The present disclosure relates generally to intravascular ultrasound (IVUS) imaging and, in particular, to receiving and focusing ultrasound information to produce an image. In various embodiments, the focusing system receives information from an array of ultrasound transducers, such as piezoelectric zirconate transducers (PZTs), capacitive micromachined ultrasonic transducers (CMUTs), and/or piezoelectric micromachined ultrasound transducers (PMUTs). The focusing system processes the data to produce an ultrasound image and may also perform various clutter reduction techniques to remove ultrasound artifacts. The system is suitable for use in a variety of applications including intravascular ultrasound. For example, some embodiments of the present disclosure provide an IVUS imaging system particularly suited to imaging a human blood vessel.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device includes one or more ultrasound transducers arranged at a distal end of an elongate member. The elongate member is passed into the vessel thereby guiding the transducers to the area to be imaged. Once in place, the transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducers and passed along to an IVUS imaging system. The imaging system processes the received ultrasound echoes to produce a cross-sectional image of the vessel where the device is placed.

There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. In side-looking rotational devices, the transducer element is oriented such that the ultrasound beam propagates generally perpendicular to the longitudinal axis of the device. In forward-looking rotational devices, the transducer element is pitched towards the distal tip so that the ultrasound beam propagates more towards the tip, in some devices, being emitted parallel to the longitudinal centerline. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the tissue, vessel, heart structure, etc. from a sequence of pulse/acquisition cycles occurring during a single revolution of the transducer.

In contrast, solid-state IVUS devices utilize a scanner assembly that includes an array of ultrasound transducers connected to a set of transducer controllers. In side-looking and some forward-looking IVUS devices, the transducers are distributed around the circumference of the device. In other forward-looking IVUS devices, the transducers are a linear array arranged at the distal tip and pitched so that the ultrasound beam propagates closer to parallel with the longitudinal centerline. The transducer controllers select transducer sets for transmitting an ultrasound pulse and for receiving the echo signal. By stepping through a sequence of transmit-receive sets, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the imaging system with a simple electrical cable and a standard detachable electrical connector.

Owing to a variety of acoustic and device characteristics, both rotational and solid-state technologies are prone to artifacts and distortions that affect the resulting image. For example, the tendency of ultrasound pressure waves to radiate outward in many directions rather than being confined to a narrow beam may result in a transceiver detecting echoes from structures at oblique angles. Ultrasound transducers also tend to produce side lobes, secondary ultrasound pressure waves that may produce additional unwanted echo data. Synthetic aperture solid-state devices may also exhibit grating lobes caused by constructive and destructive interference from neighboring transducers. For non-sparse targets (e.g., tissue), main lobes, side lobes, and grating lobes all add upon each other in a complex acoustic interplay. The undesirable acoustic effects from these and other causes may reduce the contrast, clarity, and resolution of the resulting ultrasound image and may complicate the diagnostic process. Of course, these effects are not limited to intravascular ultrasound and occur in external ultrasound, transesophageal echo, and other ultrasound systems.

While existing ultrasound imaging systems have proved useful, there remains a need for improvements in the recognition and suppression of imaging artifacts. Doing so may reduce, clarify, or even eliminate the speckle noise that is characteristic of many solid-state designs. Even where noise is not completely eliminated, any clarification of clutter is often advantageous. In addition, artifact suppression may also reduce more subtle errors that cause a real structure to have an incorrect echo intensity. As echo intensity is important to determinations such as tissue characterization, tissue boundary/border detection, distance and/or area measurements, artifact suppression may noticeably improve diagnostic accuracy. Accordingly, the need exists for improved systems and techniques for identifying and removing ultrasound artifacts.

SUMMARY

Embodiments of the present disclosure provide an ultrasound focusing engine with clutter identification and reduction, which may be used in applications such as a solid-state intravascular ultrasound imaging system.

In some embodiments, an ultrasound processing system is provided. The system comprises an interface operable to receive A-line signal data and a focusing engine communicatively coupled to the interface and operable to perform a focusing process on the received A-line signal data to produce focused A-line signal data. The system further comprises a coherency unit communicatively coupled to the interface and an adjustment unit communicatively coupled to the coherency unit. The coherency unit is operable to determine a measurement of coherency of the received A-line signal data, and the adjustment unit is operable to determine an adjustment to the focused A-line signal data based on the measurement of coherency. The adjustment may be a function of the measurement of coherency and/or the magnitude (amplitude) of the focused A-line signal data. The system further comprises a compensation unit communicatively coupled to the focusing engine and operable to apply the adjustment to the focused A-line signal data. In some such embodiments, the measurement of coherency is an indication of artifacts within the received A-line signal data, and the adjustment is determined to suppress the artifacts. In some such embodiments, the measurement of coherency is based on at least one of: a sign or a phase angle of the received A-line signal data.

In some embodiments, a method is provided. The method includes receiving A-line data and corresponding focused A-line data and determining a coherence metric of the A-line data across A-lines of an aperture of the focused A-line data. A clutter-reducing adjustment is determined for the focused A-line data based on the coherence metric, and the clutter-reducing adjustment is applied to the focused A-line data to obtain clutter-reduced A-line data. An ultrasound image is formed from the clutter-reduced A-line data. In some embodiments, the applying of the clutter-reducing adjustment is performed based on the coherence metric exceeding a threshold. In some embodiments, the method further includes determining a magnitude of the focused A-line data and the clutter-reducing adjustment for the focused A-line data is determined further based on the magnitude. In some such embodiments, the clutter-reducing adjustment is directly proportional to the magnitude. In some embodiments, the clutter-reducing adjustment is a function of both the magnitude of the focused A-line data and the coherence metric.

In further embodiments, a method of clutter reduction is provided. The method includes receiving ultrasound data and determining an indication of artifacts in the ultrasound data based on coherence of the ultrasound data. A focusing process is performed on the ultrasound data to produce focused ultrasound data, and a gamma correction is applied to the focused ultrasound data based on the indication of artifacts to suppress an effect of the artifacts. In some such embodiments, the coherence of the ultrasound data is determined based on at least one of: a sign or a post-time-of-flight adjusted phase angle of the ultrasound data. In some embodiments, the coherence of the ultrasound data is determined by accumulating a sign value total of the ultrasound data and normalizing the sign value total based on a number of A-lines in an aperture of the focused ultrasound data. In such embodiments, the coherence may be based on the normalized sign value total. In some embodiments, the coherence of the ultrasound data is determined by accumulating a phase angle total of the ultrasound data and normalizing the phase angle total based on a number of A-lines in an aperture of the focused ultrasound data. In such embodiments, the coherence may be based on the normalized phase angle total.

Some embodiments of the present disclosure utilize the coherence of the ultrasound data as measured between different A-lines of an aperture to determine the prevalence of side lobe, grating lobe, and other artifacts. Many types of artifacts are characterized by incoherence across A-lines, and in some embodiments, focused ultrasound data with a relatively high degree of incoherence undergoes a clutter-reduction technique. The clutter-reduction technique determines an amount to adjust focused ultrasound values based on a set of coherence metrics referred to as a clutter map. The adjustment amount may be further modified based on the magnitude of the focused ultrasound value being adjusted. In an embodiment, the adjustment amount is directly proportional to the magnitude of the focused ultrasound data to which it is to be applied. In this way, the system and techniques of the present disclosure can be used to reduce artifacts, improve image fidelity, increase apparent resolution, and enhance image analysis such as tissue classification. In some embodiments, the techniques herein carefully control the amount of clutter reduction to avoid completely eliminating tissue speckle as some degree of tissue speckle may help an operator to comprehend imaged structures. Similarly, some embodiments control the amount of clutter reduction to reduce clutter resolution without creating overly sparse tissue.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
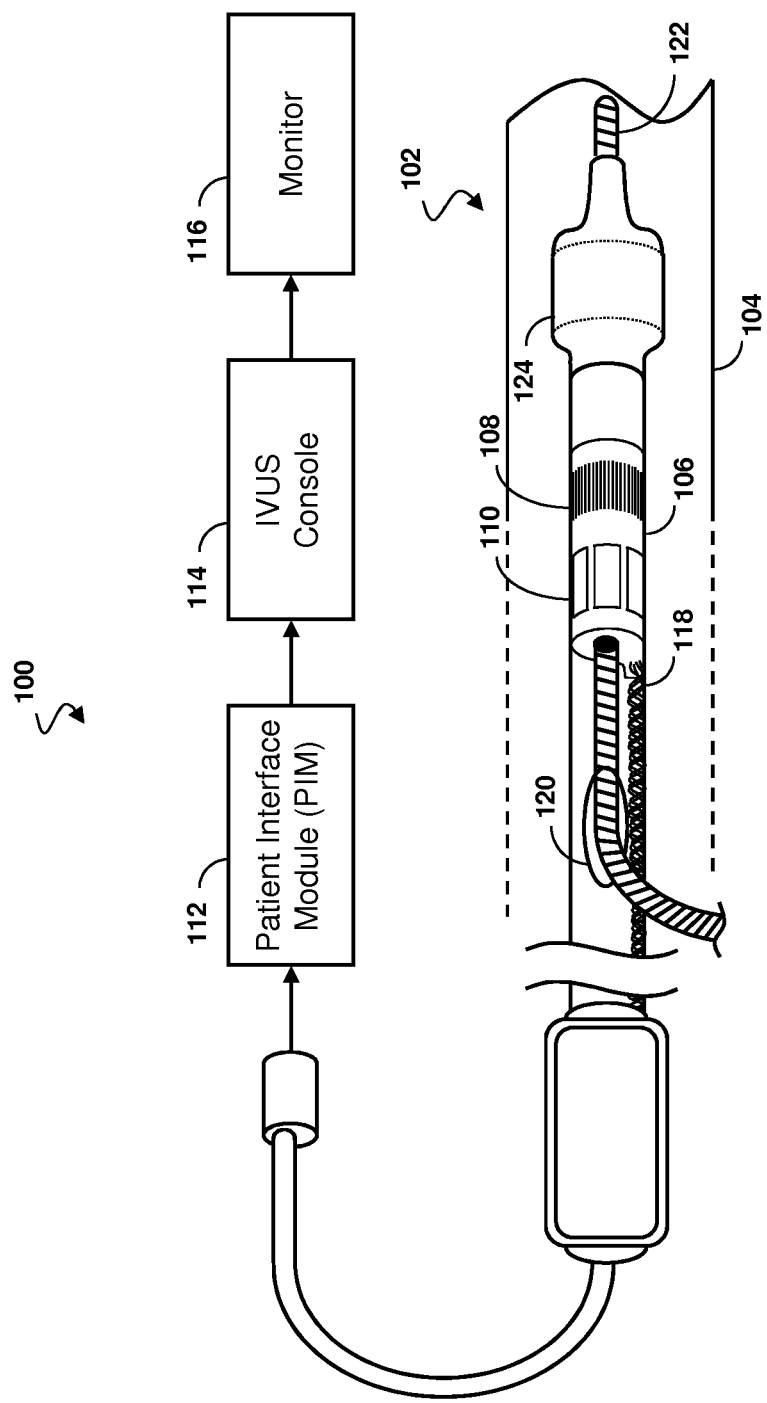
FIG. 1 is a diagrammatic schematic view of an ultrasound imaging system according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the IVUS system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound imaging system 100, such as an intravascular ultrasound system (IVUS), according to embodiments of the present disclosure. At a high level, an elongate member 102 (such as a catheter, guide wire, or guide catheter) of the imaging system 100 is advanced into a vessel 104. The distal-most end of the elongate member 102 includes a scanner assembly 106 with an array of ultrasound transducers 108 and associated control circuitry 110. When the scanner assembly 106 is positioned near the area to be imaged, the ultrasound transducers are activated and ultrasonic energy is produced. A portion of the ultrasonic energy is reflected by the vessel 104 and the surrounding anatomy and received by the transducers 108. Corresponding echo information is passed along through a Patient Interface Module (PIM) 112 to an IVUS console 114, which renders the information as an image for display on a monitor 116. In various surgical settings, patient safety requirements mandate physical and electrical isolation of the patient. Thus, if complete electrical isolation is required, the imaging system 100 may be divided into the PIM 112 and the IVUS console 114 with an optical, RF, or other non-conductive link for communication between the two. In less stringent environments, conductive communication links and/or power couplings may extend between the two. Moreover, in some embodiments, the PIM 112 and IVUS console 114 are collocated and/or part of the same system, unit, chassis, or module. The allocation of image processing tasks between the PIM 112 and the IVUS console 114 is merely arbitrary.

The imaging system 100 may use any of a variety of ultrasonic imaging technologies. Accordingly, in some embodiments of the present disclosure, the imaging system 100 is a solid-state IVUS imaging system incorporating an array of piezoelectric transducers fabricated from lead-zirconate-titanate (PZT) ceramic. In some embodiments, the system 100 incorporates capacitive micromachined ultrasonic transducers (CMUTs), or piezoelectric micromachined ultrasound transducers (PMUTs).

In some embodiments, the imaging system 100 includes some features similar to traditional solid-state IVUS system, such as the EagleEye® catheter available from Volcano Corporation and those disclosed in U.S. Pat. No. 7,846,101 hereby incorporated by reference in its entirety. For example, the elongate member 102 includes the ultrasound scanner assembly 106 at a distal end of the member 102, which is coupled to the PIM 112 and the IVUS console 114 by a cable 118 extending along the longitudinal body of the member 102. The cable 118 caries control signals, echo data, and power between the scanner assembly 106 and the remainder of the imaging system 100.

In an embodiment, the elongate member 102 further includes a guide wire exit port 120. The guide wire exit port 120 allows a guide wire 122 to be inserted towards the distal end in order to direct the member 102 through a vascular structure (i.e., a vessel) 104. Accordingly, in some instances the IVUS device is a rapid-exchange catheter. In an embodiment, the elongate member 102 also includes an inflatable balloon portion 124 near the distal tip. The balloon portion 124 is open to a lumen that travels along the length of the IVUS device and ends in an inflation port (not shown). The balloon 124 may be selectively inflated and deflated via the inflation port.

The PIM 112 facilitates communication of signals between the IVUS console 114 and the elongate member 102 to control the operation of the scanner assembly 106. This includes generating control signals to configure the scanner, generating signals to trigger the transmitter circuits, and/or forwarding echo signals captured by the scanner assembly 106 to the IVUS console 114. With regard to the echo signals, the PIM 112 forwards the received signals and, in some embodiments, performs preliminary signal processing prior to transmitting the signals to the console 114. In examples of such embodiments, the PIM 112 performs amplification, filtering, and/or aggregating of the data. In an embodiment, the PIM 112 also supplies high- and low-voltage DC power to support operation of the circuitry within the scanner assembly 106. The PIM 112 may also perform some, all, or none of the functions attributed to the IVUS console 114 such as processing the echo data to create an ultrasound image.

The IVUS console 114 receives the echo data from the scanner assembly 106 by way of the PIM 112 and performs any remaining processing of the data to create an image of the tissue surrounding the scanner assembly 106. The console 114 may also display the image on the monitor 116.

The ultrasound imaging system 100 may be utilized in a variety of applications and can be used to image vessels and structures within a living body. Vessel 104 represents fluid filled or surrounded structures, both natural and man-made, within a living body that may be imaged and can include for example, but without limitation, structures such as: organs including the liver, heart, kidneys, as well as valves within the blood or other systems of the body. In addition to imaging natural structures, the images may also include imaging man-made structures such as, but without limitation, heart valves, stents, shunts, filters and other devices positioned within the body.

Figure 2:
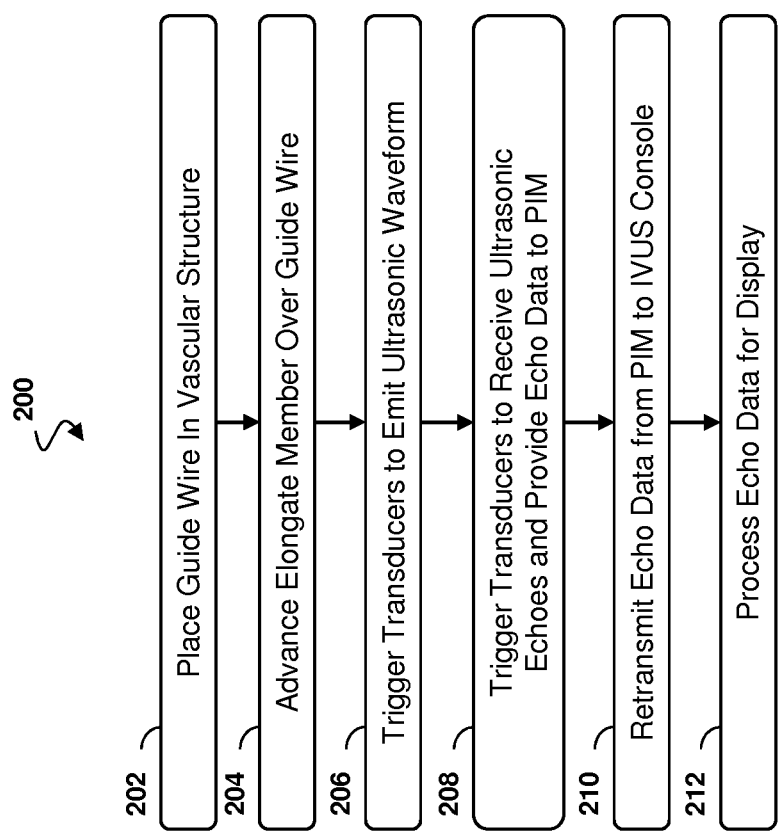
FIG. 2 is a flow diagram of a method of utilizing the imaging system according to embodiments of the present disclosure.

FIG. 2 is a flow diagram of a method 200 of utilizing the imaging system 100 according to embodiments of the present disclosure. It is understood that additional steps can be provided before, during, and after the steps of method 200, and that some of the steps described can be replaced or eliminated for other embodiments of the method.

Referring block 202 of FIG. 2 and referring still to FIG. 1, in an illustrative example of a typical environment and application of the system, a surgeon places a guide wire 122 in the vessel 104. The guide wire 122 is threaded through at least a portion of the distal end of the elongate member 102 either before, during, or after placement of the guide wire 122. Referring to block 204 of FIG. 2, once the guide wire 122 is in place, the elongate member 102 is advanced over the guide wire. Additionally or in the alternative, a guide catheter is advanced in the vessel 104 in block 202 and the elongate member 102 is advanced within the guide catheter in block 204.

Referring to block 206, once positioned, the scanner assembly 106 is activated. Ultrasound imaging is described in more detail with reference to FIGS. 3-5, but at a high level, signals sent from the PIM 112 to the scanner assembly 106 via the cable 118 cause transducers within the assembly 106 to emit a specified ultrasonic waveform. The ultrasonic waveform is reflected by the vessel 104 and the surrounding anatomy. Referring to block 208 of FIG. 2, the reflections are received by the transducers within the scanner assembly 106 and are amplified for transmission via the cable 118. The echo data is placed on the cable 118 and sent to the PIM 112. The PIM 112 amplifies the echo data and/or performs preliminary pre-processing, in some instances. Referring to block 210, the PIM 112 retransmits the echo data to the IVUS console 114. Referring to block 212, the IVUS console 114 aggregates and assembles the received echo data to create an image of the vessel 104 for display on the monitor 116. In some exemplary applications, the IVUS device is advanced beyond the area of the vessel 104 to be imaged and pulled back as the scanner assembly 106 is operating, thereby exposing and imaging a longitudinal portion of the vessel 104. To ensure a constant velocity, a pullback mechanism is used in some instances. A typical withdraw velocity is 0.5 mm/s. In some embodiments, the member 102 includes an inflatable balloon portion 124. As part of a treatment procedure, the device may be positioned adjacent to a stenosis (narrow segment) or an obstructing plaque within the vessel 104 and inflated in an attempt to widen the restricted area of the vessel 104.

Figure 3:
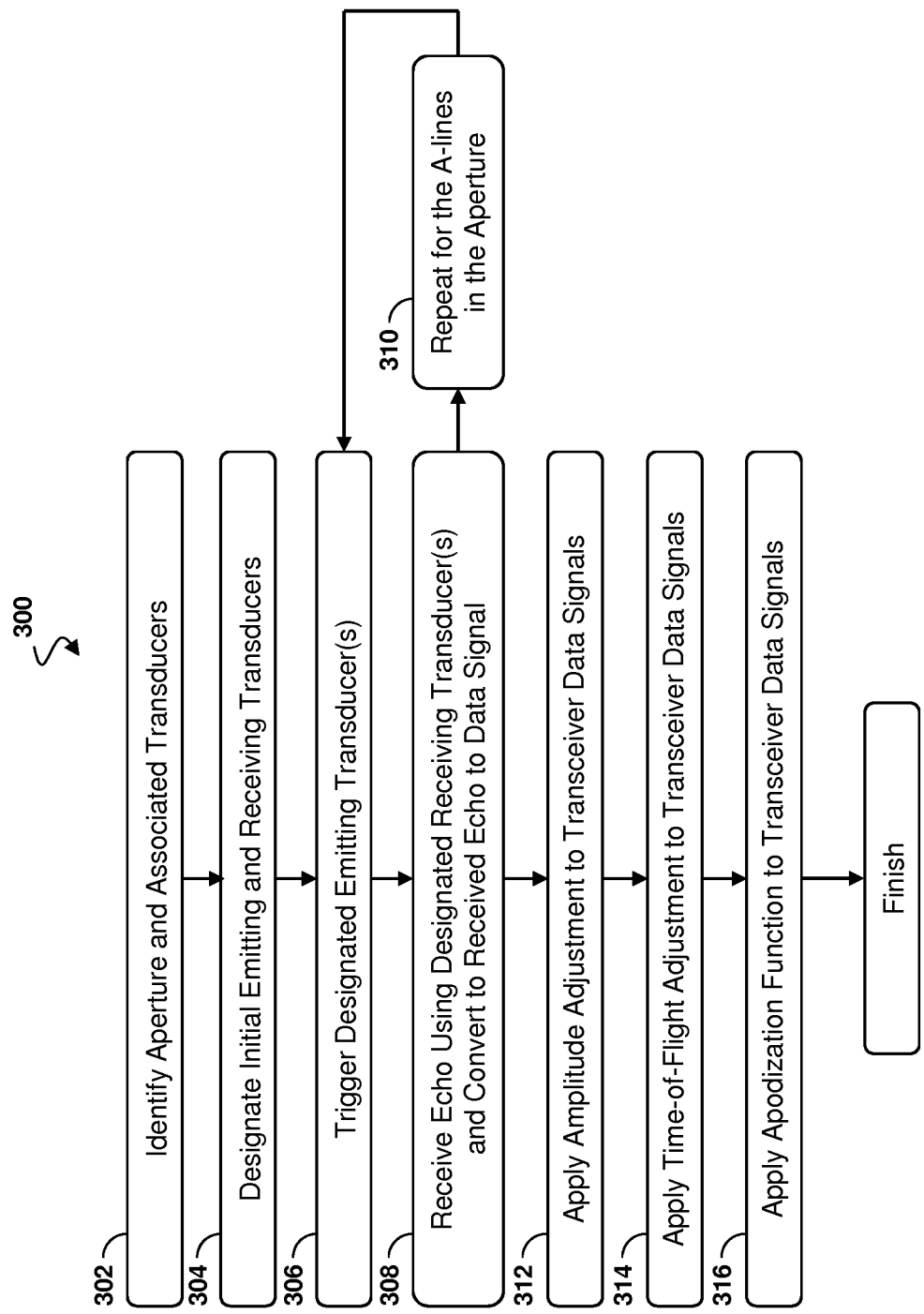
FIG. 3 is a flow diagram of a method of generating ultrasound imaging data according to embodiments of the present disclosure.
Figure 4:
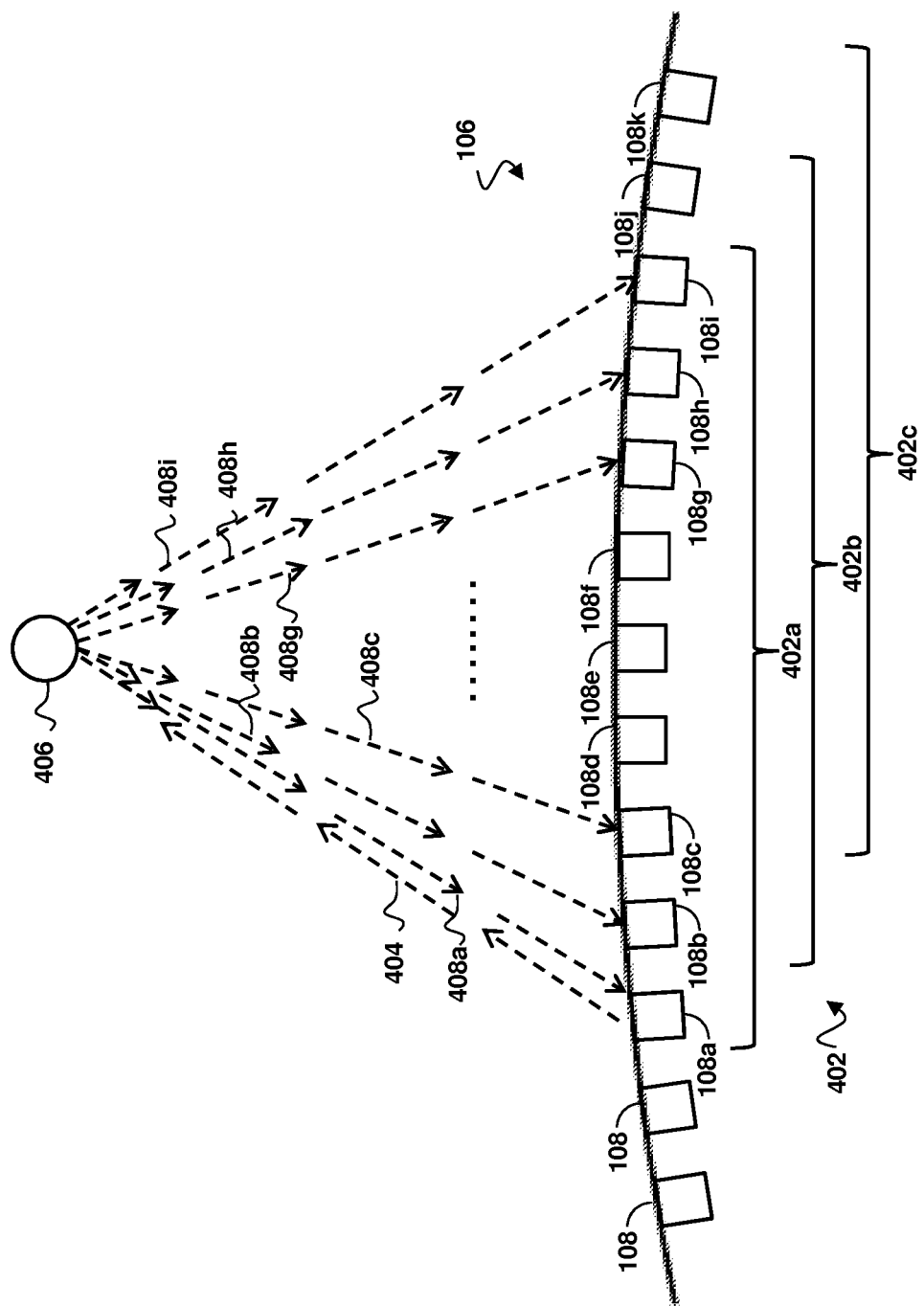
FIG. 4 is a radial cross-sectional view of a portion of a scanner assembly of an imaging system according to embodiments of the present disclosure.
Figure 5:
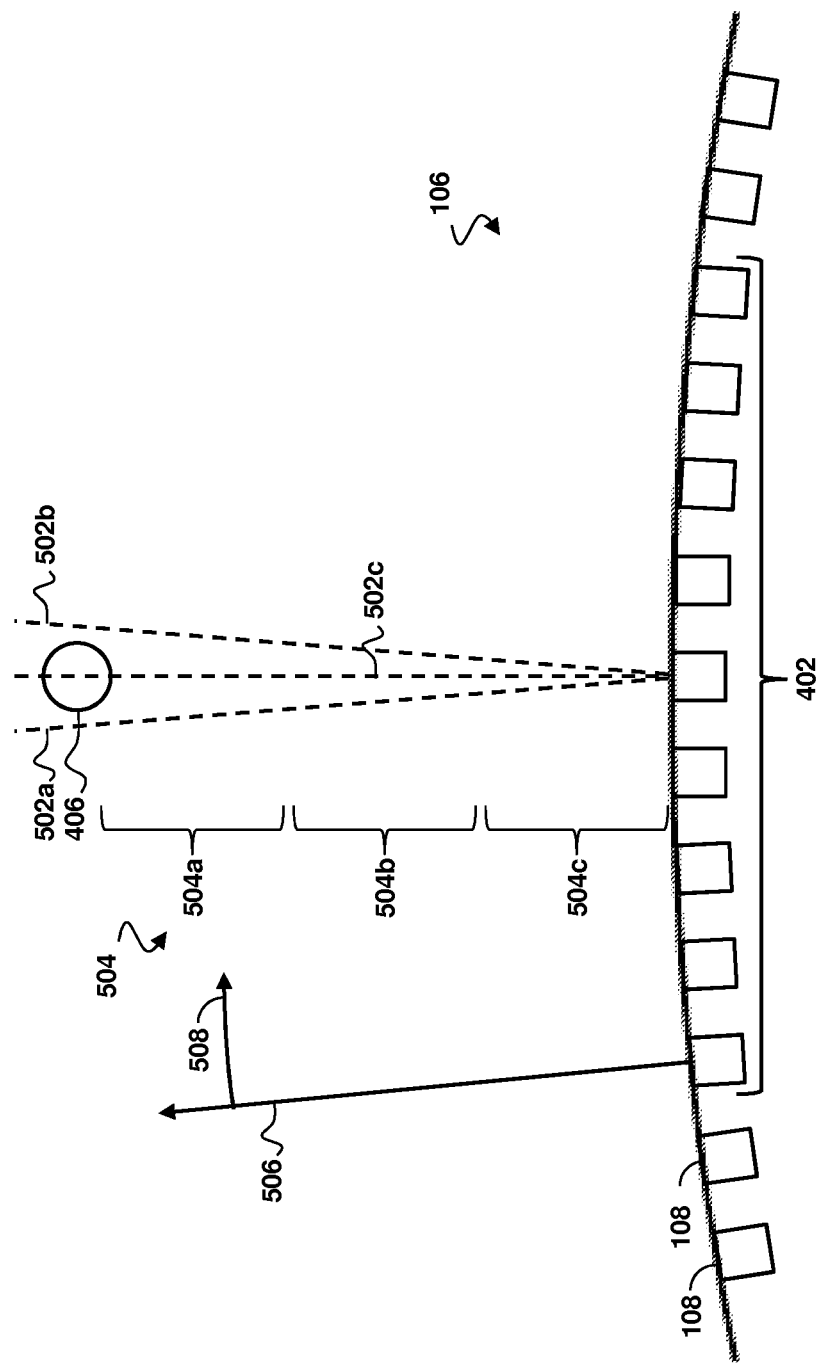
FIG. 5 is a cross-sectional view of a focused aperture of a scanner assembly according to embodiments of the present disclosure.

The system 100, and in particular the elongate member 102, is designed to provide high-resolution imaging from within narrow passageways. A method of collecting and processing ultrasound imaging data is described with reference to FIGS. 3-5. FIG. 3 is a flow diagram of a method 300 of generating ultrasound imaging data according to embodiments of the present disclosure, which may be performed during the surgical method 200 of FIG. 2. It is understood that additional steps can be provided before, during, and after the steps of method 300, and some of the steps described can be replaced or eliminated for other embodiments of the method. FIG. 4 is a radial cross-sectional view of a portion of a scanner assembly 106 according to embodiments of the present disclosure. FIG. 5 is a cross-sectional view of a focused aperture 402 of a scanner assembly 106 according to embodiments of the present disclosure.

Referring first to FIG. 4, the scanner assembly 106 houses an array of transducers 108, thirteen of which are illustrated. The transducers 108 are grouped into apertures 402, including apertures 402a, 402b, and 402c. During an ultrasound firing, some transducers 108 of an aperture 402 will emit an ultrasound waveform, while some transducers 108 of the aperture 402 will listen for echoes produced by the waveform. Transducers 108 may operate as both emitters and receivers during the same firing. More than one transducer 108 may be activated concurrently in order to produce the ultrasound waveform. Firing transducers as a group may create a stronger ultrasonic transmission. Particularly in, but not limited to, embodiments using relatively small emitting transducers and/or embodiments imaging relatively long distances, a stronger emission improves the signal-to-noise ratio. Similarly, in some embodiments, a plurality of receiving transducers is set to receive as a group. The group of transducers may produce a stronger electrical potential with a better imaging characteristics than individual transducers acting alone.

In some embodiments, each transducer 108 may be part of one or more apertures 402. For example, transducer 108c is included in apertures 402a, 402b, and 402c. By way of non-limiting example, in the illustrated embodiment, each aperture 402 contains nine transducers 108. Other aperture widths are contemplated. For example, further embodiments have apertures 402 containing 8, 10, 12, 14, 16, or 32 transducers 108. In an embodiment, an aperture 402 contains 128 transducers 108.

Referring to block 302 of FIG. 3 and referring still to FIG. 4, an aperture 402 and its corresponding transducers 108 are identified and selected for ultrasound data acquisition. The identifying process may include determining the relative placement of transducers 108 within the aperture 402. In block 304, an initial group of emitting and receiving transducers is designated. Groupings of emitting and receiving transducers are referred to as A-lines. Within an A-line, more than one emitting transducer and more than one receiving transducer may be configured to act together. Furthermore, in some embodiments, a transducer may be designated as both an emitting and a receiving transducer. Accordingly, in an exemplary firing, transducer 108a is both the initial emitting transducer and the initial receiving transducer.

In block 306, the designated emitting transducer(s) (in the current example, transducer 108a) are triggered to emit ultrasonic energy. A portion of the ultrasonic energy (e.g., the portion directed along the line indicated by arrows 404) is reflected by a target structure 406 located in the environment surrounding the scanner assembly 106. In block 308, the designated receiving transducer (in the current example, transducer 108a) or transducers receive the reflected ultrasonic echo (indicated by arrows 408a-408i, of which arrows 408d-408f are omitted for clarity). For the purposes of this disclosure, the act of receiving by a transducer may include experiencing an energy impulse such as an ultrasonic echo, converting the received impulse into a signal such as an electric potential, transmitting the converted signal, measuring the converted signal, and/or other suitable receiving steps.

Referring to block 310, the transmit and receive process may be repeated for each A-line (emitter/receiver combination) of the aperture. The order in which the A-lines of the aperture are used to collect data may be specified by a walk pattern of the aperture. An exemplary walk pattern, which may be designated a forward walk, advances transducers in an arbitrary first direction (e.g., from transducer 108a to 108b to 108c). A backward walk advances transducers in a direction opposite the first direction (e.g., from transducer 108c to 108b to 108a). Other walk patterns utilize more than one direction, skip transducers, repeat transducers, group transducers and/or operate according to any other suitable pattern.

In some embodiments, the number of A-line firings is reduced by assuming that A-line data exhibits a reciprocal nature. In other words, a signal emitted by transducer 108a and received by transducer 108i may be a suitable substitute for a signal emitted by transducer 108i and received by transducer 108a. Thus, in some such embodiments, only one A-line firing for each reciprocal A-line pair is performed.

As the echo data is being collected in blocks 304-310, it may undergo a mathematical focusing process. Focusing improves image quality by adjusting and combining data collected from the A-line transducer groups. The effect of focusing is to combine the A-line data into a dataset that simulates a narrow beam-width emission/reception from a location within the aperture 402 and received at a location on the scanner assembly 106, as seen in FIG. 5, regardless of whether transducers 108 actually exist at these locations or whether such a narrow beam-width emission/reception could be produced. In some embodiments, more than one focused A-line is determined per aperture 402. The different focused A-lines may be directed at different angles relative to the surface of the scanner assembly 106. For example, focusing may produce data for A-lines 502a, 502b, and 502c. These different focused A-lines may be referred to as different flavors of focused A-line data.

In some embodiments, the focusing calculations are range sensitive. For example, a given focused A-line (e.g., A-line 502a) may be calculated using one set of factors for range 504a, another set for 504b, and another for 504c. In further non-limiting examples, a given focused A-line is calculated for other numbers of ranges 504 including 2, 4, 5, 6 and 9. In an embodiment, the number of ranges 504 corresponds to the number of samples collected for a measured (not focused) A-line. Other suitable numbers of ranges are provided for. Thus, focusing may include sets of calculations divided by range, flavor, and/or other aspects of the focused A-line to be produced.

Referring to block 312, at any time prior to or during focusing, an amplitude adjustment may be performed on the echo data. In some embodiments, the amplitude adjustment accounts for sensitivity and other characteristics of the transducers. For example, a transducer may have reduced sensitivity to signals directed at oblique angles. Thus, a directional amplification factor may be determined based on the receiving transducer's location relative to the emitting transducer. In a further example, an adjustment may be applied to correct for a less-sensitive transducer such as one that may result from a manufacturing variance.

Referring to blocks 314 and 316, the process of focusing may include space-time alignment of data (radial focusing, the radial direction indicated by arrow 506) as well as spatial alignment of data (azimuthal focusing, the azimuthal direction indicated by arrow 508). The first type of alignment, space-time alignment, may include time-of-flight adjustment. Due to different flight paths between A-lines, received echoes may arrive at the transducers at different times. Referring to block 314, a time-of-flight adjustment shifts the A-line data signals in time to align with the signals of the other A-lines within the aperture.

Referring to block 316, an apodization function is applied to the data signal before and/or after the time-of-flight adjustment of block 312. Apodization is a specific type of amplitude weighting and may be used to reduce grating and side lobe effects and other artifacts from the imaging process. Side lobes occur in ultrasound imaging due to the ultrasound beam geometry and are determined by the frequency and aperture size and shape. Grating lobes are caused by constructive and destructive interference from neighboring transducers 108 and apertures 402, which result from blind spots on the scanner assembly 106 where no transducer 108 is present. Apodization may include tapering off the amplitude of a received response on either side of a window of time. This emphasizes the response during the peak of the window, which may be more likely to be produced by a main lobe of an ultrasound signal rather than a grating lobe or side lobe. Exemplary apodization weightings include Boxcar, Hann, Hamming, Taylor, cosine, root-raised-cosine, and half-cosine window functions.

Figure 6:
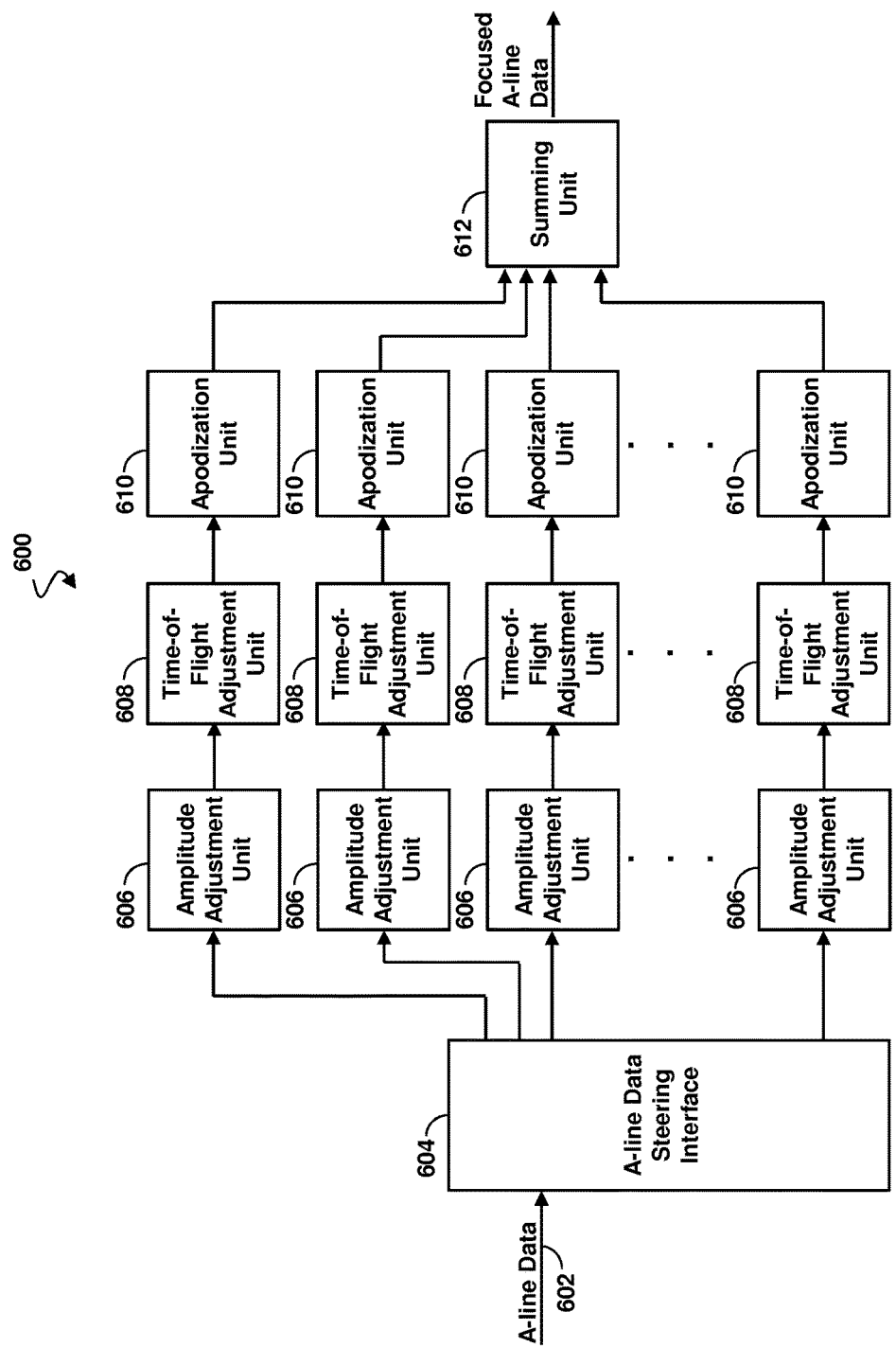
FIG. 6 is a schematic of a focusing system according to embodiments of the present disclosure.

FIG. 6 is a schematic of a focusing system 600 according to embodiments of the present disclosure. Portions of the focusing system 600 may be incorporated into an IVUS console 114, a Patient Interface Module (PIM) 112, and/or other components of an imaging system 100. In various embodiments, the focusing system 600 focuses A-line data from the transducer 108 within an aperture 402 to produce a focused dataset for the aperture 402. Focusing system 600 receives A-line data 602 at an A-line data steering interface 604. In some embodiments, the interface 604 receives the A-line data 602 from a scanner assembly 106. In some such embodiments, the A-line interface 604 receives data directly from transducers 108 of the scanner assembly 106. In some embodiments, the A-line interface 604 receives data from a memory subsystem (e.g., a data buffer), an analog-to-digital converter, an analog and/or digital amplifier, a filter, a signal conditioner, and/or other suitable interface systems Likewise, the A-line interface 604 may include any of these elements.

The A-line data steering interface 604 directs the received data to the appropriate amplitude adjustment unit 606. The amplitude adjustment units 606 may perform an amplitude adjustment based on transducer characteristics such as an adjustment of signal bandwidth through filters such as matched filters. In some embodiments, the amplitude adjustment accounts for sensitivity and other characteristics of the transducers. For example, a transducer may have reduced sensitivity to signals directed at oblique angles. Thus, a directional amplification factor may be applied based on the receiving transducer's location relative to the emitting transducer. In a further example, an adjustment may be applied to correct for a less-sensitive transducer such as one that may result from a manufacturing variance. The amplitude adjustment units 606 provide the adjusted A-line data to the time-of-flight (TOF) adjustment units 608.

The time-of-flight adjustment units 608 align the A-line data in time, which improves resolution, and with careful selection, can reduce grating lobes, side lobes, and other artifacts. In the illustrated embodiment, the focusing system 600 includes a time-of-flight adjustment unit 608 for each A-line in the aperture, although only four are illustrated for the sake of clarity. Other embodiments incorporate as few as one time-of-flight adjustment unit 608. The time-of-flight adjustment unit or units 608 align the A-line data by shifting the signal in time according to an offset. In some embodiments, the particular offsets applied by the units 608 are determined based on a geometry of the scanner assembly 106 (e.g., degree of curvature, transducer spacing, distance between emitter and receiver, length of signal lines, etc.), a characteristic of a transducer (e.g., firing delay, sensitivity etc.), a characteristic of an aperture (e.g., width, location on the transducer complex, beam-steer angle, etc.), and/or other relevant factors that affect arrival time. In some embodiments, such as when a focused A-line is broken up into more than one calculation based on a focal range 504 or flavor, discrete time-of-flight offsets are supplied for each particular focal range 504 or flavor. In some embodiments, time-of-flight offsets are determined by analysis of the incoming A-line data through a method such as peak detection either in addition to or as a replacement for utilizing pre-determined values. After the offset is applied, the aligned A-line data is supplied to the apodization units 610.

Apodization units 610 apply another set of amplitude weightings to further correct for grating lobe effects, side lobe effects, and other artifacts. The weightings applied by the apodization units 610 to reduce these effects typically taper off the amplitude of a received response on either side of a window of time and may be derived from apodization functions such as a Boxcar, Hann, Hamming, Taylor, cosine, root-raised-cosine, half-cosine window function and/or other suitable apodization function. The resulting aligned and apodized data is provided to a summing unit 612, which adds the data from the unfocused A-lines to produce focused A-line data for the aperture. The summing unit 612 may perform incoherent beamforming by summing the magnitude of the apodized and time-of-flight-adjusted data and/or may perform coherent beamforming by summing the signed apodized and time-of-flight-adjusted data. In general, an incoherent beamforming result may be more accurate but may be blurrier than a corresponding coherent beamforming result. The techniques of the present disclosure apply equally to incoherent and coherent beamforming.

Despite the general effectiveness of the apodization units 610 in reducing side lobe effects, grating lobe effects, and other distortions, some artifacts may still remain in the focused ultrasound data. For the purposes of this disclosure, clutter artifacts include any ultrasound data greater than or less than that produced by the tissue or structures directly in line with the ideal focused A-line. For example, clutter artifacts include "speckle noise", random variations in intensity that resemble static on an ultrasound image. A more subtle clutter artifact occurs when grating lobe or side lobe echoes from one target interfere with the main lobe echoes of a second target. This may cause the second target to appear stronger or weaker in intensity in a manner that is difficult for an operator to detect. When the clutter intensity is low, it may be a mere annoyance. However, when the clutter intensity becomes greater, it may be misinterpreted as valid data, leading to errors in measurement and potential misdiagnoses.

Figure 7:
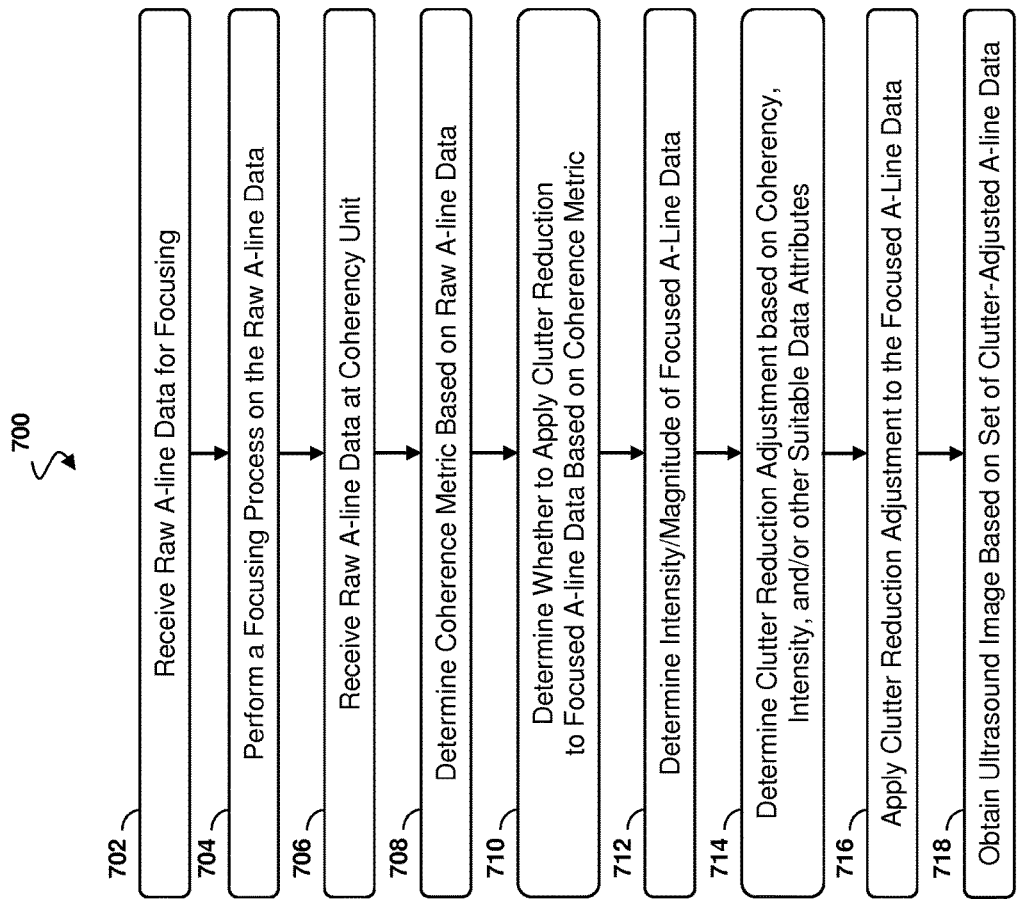
FIG. 7 is a flow diagram of the method of clutter reduction of ultrasound data according to embodiments of the present disclosure.
Figure 8:
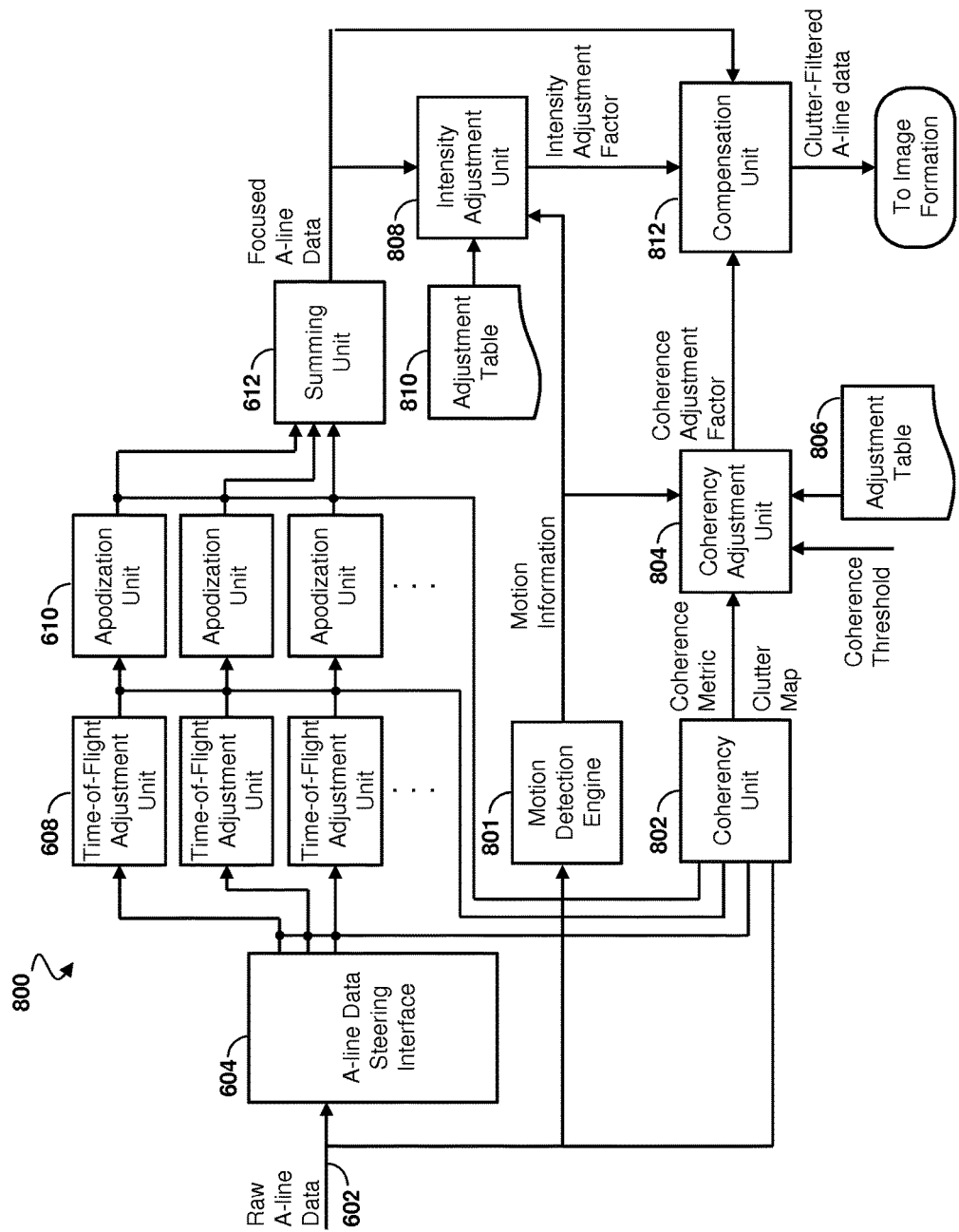
FIG. 8 is a schematic of a focusing system operable to perform the method of clutter reduction according to embodiments of the present disclosure.

To correct these distortions and others, a clutter-reduction technique may be performed on the ultrasound data before and/or after focusing. An exemplary clutter-reduction technique is described with reference to FIGS. 7-8. In some embodiments, the clutter-reduction technique recognizes differences in signal qualities that are characteristic of clutter and produces a clutter map that quantifies the effect on focused A-line data values at a number of positions relative to the scanner assembly. The clutter map is then used to compensate the focused data to reduce the clutter. FIG. 7 is a flow diagram of the method 700 of clutter reduction of ultrasound data according to embodiments of the present disclosure. It is understood that additional steps can be provided before, during, and after the steps of method 700, and that some of the steps described can be replaced or eliminated for other embodiments of the method. FIG. 8 is a schematic of a focusing system 800 operable to perform the method 700 of clutter reduction according to embodiments of the present disclosure. Portions of the focusing system 800 may be incorporated into an IVUS console 114, a Patient Interface Module (PIM) 112, and/or other components of an imaging system 100.

In many aspects, the focusing system 800 may be substantially similar to the system 600 of FIG. 6. For example, the focusing system 800 may include an A-line data steering interface 604, one or more time-of-flight adjustment units 608, one or more apodization units 610, and a summing unit 612, each substantially similar to those of system 600. The focusing system may also include a motion detection engine 801. In addition to structural focusing, ultrasound focusing systems may have the ability to detect motion. One method of determining motion in the imaged area is power flow. An example of a power flow algorithm is ChromaFlo® (a trademark of Volcano Corporation). In contrast to focusing spatial A-line data to determine reflection strength of a scatterer, a flow algorithm may use temporal A-line data to determine flow rate and spectral intensity of the scatterer. In other words, instead of focusing multiple A-lines within an aperture, a single A-line is fired and captured multiple times. The phase or amplitude change in the signal of the A-line between firings can be correlated to scatterer motion. The motion information determined by the motion detection engine 801 may be considered by the focusing system 800 when removing clutter.

Regarding clutter, it has been determined that while data produced by side lobes, grating lobes, and other distortions may have amplitudes (absolute values) that mimic those of ultrasound data caused by the main lobe in normal, clinical conditions, the distorted values are not coherent, meaning they are out of phase. In other words, the side lobes, grating lobes, and other clutter are not correlated well with each other and are not phase aligned across A-lines. These differences in coherence can be measured by determining the relative phases of the echo data across the A-lines and by other techniques of measuring coherency. In many applications, grating lobes are more coherent than side lobes, but still less coherent than main lobe data in clinical conditions.

Ultrasound is a compressive wave and includes regions of compression and regions of rarefaction. Thus, differences in phase represent different positions in the compression and rarefaction cycle. In various embodiments, these different positions are detected by calculating the phase of a transducer 108 signal and/or by using the sign term of a transducer 108 signal. In this regard, sign may be considered a rough sampling of phase. As the sensitive element of the transducer 108 (such as the diaphragm) is deflected from the neutral position by an ultrasound wave front, the orientation of the deflection, which can be used to distinguish compression from rarefaction, is represented by the sign of the transducer response. In some embodiments, the sign of the transducer data corresponds to the polarity (positive/negative) of the electrical signal produced by a transducer 108, whereas in other embodiments, the sign of the transducer data corresponds to whether the electrical signal is above or below a reference voltage produced by a biased transducer 108. Because artifacts produce raw A-line data that is less coherent, raw A-line data (before focusing) produced by side lobes, grating lobes, and other clutter has signs that vary across A-lines, while the raw A-line data produced by the main lobe has signs that are uniform across A-lines.

In other examples, the phase of the transducer 108 signal is calculated rather than relying solely on the signal sign. This is particularly useful in when the ultrasound data is converted into a baseband representation because of the ease calculating the phase from the baseband representation. When examining the phase terms, the main lobe produces A-line data that, after a time-of-flight adjustment, has a minimal phase angle sum. The precise phase angle of each A-line depends on various operational characteristics, including aperture steer angle and range, but main lobe data has a minimal phase angle with minimal variance across A-lines. Accordingly for main lobe echo data, the sum of the phase angles tends towards the average phase angle multiplied by the number of A-lines. In contrast, the side lobes and grating lobes produce A-line data that, after the time-of-flight adjustment, may have both greater phase angles and wider phase variance. Thus, the sum of the phase angles is greater than main lobe data. To further amplify this effect, the absolute value of the phase angles may be added rather than the signed phase angles. By these techniques and others, some of the embodiments that follow use the coherence of the underlying A-line data to determine the extent to which focused data value is affected by clutter and to correct it.

Referring to block 702 of FIG. 7 and to FIG. 8, the focusing system 800 receives raw (unfocused) A-line data is received for the A-lines of an aperture 402. The A-line data 602 may be received directly from transducers 108 of the scanner assembly 106 and/or from a transducer interface system such as a memory buffer, an analog-to-digital converter, an analog and/or digital amplifier, a filter, a signal conditioner, and/or from other suitable interface system component. In one such embodiment, the raw A-line data is received by an A-line data steering interface 604 substantially similar to that of FIG. 6. Referring to block 704, the focusing system 800 performs a focusing technique on the raw A-line data. The focusing technique may include any of the focusing processes described in blocks 312-316 of FIG. 3 and/or other focusing process.

Referring to block 706 of FIG. 7 and to FIG. 8, concurrent with the focusing process, a coherency unit 802 receives the raw A-line data used to calculate the focused A-line data. In subsequent processes, the coherency unit 802 uses various properties of the raw A-line data to determine a coherence metric for the focused A-line data. The coherency unit 802 may receive the raw A-line data before or after a time-of-flight adjustment is applied to the data. Accordingly, pre-time-of-flight adjusted data may be obtained at the input and/or output the A-line data steering interface 604. Pre-time-of-flight adjusted data may be obtained before or after any amplitude adjustment is applied, as a uniform amplitude adjustment alone typically does not affect coherence.

Referring to block 708, the coherency unit 802 analyzes the A-line data for coherency between A-lines, and based on the analysis, produces a coherence metric for each focused A-line data value. In some exemplary embodiments, the coherency unit 802 uses sign information of the raw A-line data to determine the coherence metric. In some such embodiments, the coherency unit 802 includes an accumulator that accumulates a running total of signs of the raw A-line data. As explained above, the sign of an A-line data value represents whether the transducer is experiencing compression or rarefaction and may be expressed by a polarity of a data signal, a variance from a reference voltage, and/or any other suitable representation.

In one example, each raw A-line data value having a first sign is assigned the same sign value (such as +1) irrespective of the magnitude of the A-line data value, while each raw A-line data value having an opposite sign is assigned an opposing sign value (such as −1) irrespective of magnitude. In the example, the coherency unit 802 adds the sign values of the raw A-line data values used to determine a focused A-line data value. The sign value total may be normalized by dividing by the number of raw A-lines used to determine the focused A-line data value in order to obtain a percentage ranging between −100% and +100%, inclusive. In some embodiments, the number of raw A-lines used to determine a focused A-line data value depends on the focal range. Fewer A-lines may be used to determine focused A-line data near the surface of the scanner assembly 106 where the aperture is smaller, while relatively more A-lines may be used to determine focused data further from the scanner assembly 106. The coherence metric may include the sign value total and/or the normalized sign value total.

In the ideal case of a single point scatterer, the normalized sign value total for a focused A-line data value obtained by a main lobe reflection of the point scatterer would be either +100% or −100%, and the normalized sign value total for a focused A-line data value produced by clutter would be 0%. However, in most applications, a vessel 104 will include enough reflective structures that each focused A-line data value will have some main lobe ultrasound data and some clutter effects. Accordingly, the coherence metric may be considered a measure of the extent to which the focused A-line data value is due to clutter artifacts.

In a further exemplary embodiment, the raw A-line data value is converted into a baseband representation during the focusing process. Put succinctly, baseband data handling downmixes a high-frequency signal such as A-line echo data by a carrier frequency, $f_C$, to produce a set of complex lower-frequency signal. In some embodiments, the downmixed data is centered at or near DC (0 Hz). Because the resulting signals have lower characteristic frequencies, digital sampling rates can be reduced and other problems associated with high frequency signal processing can be alleviated. The underlying principle is that a time varying measure signal S(t) having carrier frequency $f_C$ and phase θ(t) can be converted to baseband by determining in-phase, I(t), and quadrature, Q(t), components as follows:

$$I(t) = S(t) * \sqrt{2} \cos(2\pi f_C t)$$

$$Q(t) = S(t) * -\sqrt{2} \sin(2\pi f_C t)$$

As discussed above, coherence can be determined by the sum of the phase angles of the unfocused baseband A-line data values after the time-of-flight adjustment. In a baseband representation, phase θ(t) can be determined from the equation:

$$\theta(t) = \tan^{-1} \frac{Q(t)}{I(t)}$$

Accordingly, in some embodiments, the coherency unit 802 receives the baseband A-line data values from the output of the time-of-flight adjustment units 608 and adds the phase angles or the magnitude (absolute value) of the phase angles of the raw baseband A-line data values. In this way, the coherency unit 802 obtains a phase angle sum. A smaller phase angle sum indicates coherent data, while greater phase angle sums indicates increasing incoherence. In such embodiments, the coherence metric may be based on the relationship of the phase angle sum to the minimum phase angle sum in the focused A-line. For example, the current phase angle sum may be divided by the minimum phase angle to determine the coherency metric. In the ideal case of a single point scatterer, there is a clear discontinuity in the phase angle sums between a main lobe echo produced by the point scatterer and echo data produced by clutter. However, in most applications, a vessel 104 will include enough reflective structures that each focused A-line data value will have some main lobe ultrasound data and some clutter effects and so there is an art to distinguishing between main lobe and clutter data.

The coherence metrics and their corresponding locations in space may be referred to collectively as a clutter map. The clutter map is used to adjust the focused A-line data values in order to suppress the clutter effects in the focused data. The adjustment amount may be determined by applying a weighting function to the clutter metrics to condition the clutter map. It should be noted that in many embodiments, the focusing system 800 does not store or retain a complete clutter map or conditioned clutter map at any one time. For example, the coherence metrics of the clutter map may be determined as the focused A-line data values are determined. In some such embodiments, each coherence metric is applied to the respective focused A-line data and discarded shortly thereafter. Additionally or in the alternative, all or part of the clutter map or conditioned clutter map may be stored by the focusing system 800 in any suitable format including a linked list, a tree, a table such as a hash table, an associative array, a state table, a flat file, a relational database, a bitmap, and/or other memory structure.

In order to suppress artifacts, an adjustment is determined for the focused A-line data based on the coherency metrics and/or the intensity (i.e., magnitude) of the focused A-line data. In some embodiments, clutter reduction is performed on each focused A-line data value. However, in some applications, it is advantageous to only apply clutter reduction to those focused A-line data values that exhibit a certain amount of artifacts. In particular, overly aggressive clutter reduction can result in sparse images that lack tissue speckle used to distinguish tissue from other structures or empty space. Selective clutter reduction may better preserve conventional tissue appearance. Accordingly, referring to block 710, a coherency adjustment unit 804 makes a determination of whether to apply clutter reduction to a focused A-line data value based on the coherence metric and a coherence threshold. In an embodiment, an exemplary coherence threshold specifies that clutter reduction is to be performed on those focused A-line data values having corresponding coherency metrics with normalized sign value totals between about −70% and +70%. In the example, clutter reduction is not performed on focused A-line data values having corresponding coherency metrics with normalized sign values greater than about +70% or less than about −70%. In practice, the coherence threshold may depend on range, beam angle, motion information, and/or other suitable information. For example, as fast moving tissue produces less coherent data than slower moving tissue, the clutter reduction threshold may be modified so that clutter reduction is not applied to the less coherent data that is nevertheless still main lobe data.

For those focused A-line data values selected for clutter reduction, an adjustment is determined that is a function of the coherency and/or the intensity of the focused A-line data. In the illustrated embodiment, the focusing system 800 includes two adjustment units (coherency adjustment unit 804 and intensity adjustment unit 808) used to determine the adjustment amount, although in further embodiments, the two adjustment units are merged. Referring to block 712, the coherency adjustment unit 804 determines a coherency-based adjustment factor for a focused A-line data value based on the corresponding coherence metric in the clutter map. As the coherence metric represents the extent to which the focused A-line data value is affected by artifacts, the coherency-based adjustment amount may be directly correlated with the coherence metric. However, the two need not exhibit a purely linear relationship with the coherence metric. In many embodiments, the adjustment amount is a polynomial of the form:

$$A_C = \sum_{i=0}^{m} \lambda_i C^i$$

where $A_C$ represents the coherency-based adjustment amount, $\lambda_i$ represents a normalizing constant for a polynomial order of i based on range, beam angle, motion information, and/or other factors, $C^i$ represents the value of the coherence metric (e.g., sign value total, normalized sign value total, normalized phase angle, etc.) raised to the power of i, and m is any arbitrary value. $A_C$ may also depend on the intensity adjustment, $A_I$, described in more detail below. In some embodiments, coherency-based adjustment values are determined ahead of time and stored in an adjustment table 806, which may be represented in any suitable memory format including a linked list, a tree, a table such as a hash table, an associative array, a state table, a flat file, a relational database, a bitmap, and/or other memory structure. Accordingly, the determination of block 712 may include the coherency adjustment unit 804 querying the adjustment table 806 based on the coherence metric.

It has been also determined that clutter reduction can be further improved by tuning the amount of clutter reduction applied based on the magnitude of the focused A-line data value. In some examples, increasing the amount of clutter reduction applied when a focused A-line data value is greater produces a more accurate image. Accordingly, referring to block 714, the intensity adjustment unit 808 receives focused A-line data values and determines an intensity-based adjustment for those focused A-lines undergoing clutter reduction based on the magnitude of the respective focused value. Doing so may avoid overly aggressive clutter reduction that can result in sparse images that lack tissue speckle used to distinguish tissue from other structures or empty space.

Similar to the coherency-based adjustment, the intensity-based adjustment may have a linear relationship to the magnitude of the focused A-line data value and/or may have a polynomial relationship of the form:

$$A_I = \sum_{i=0}^{m} \lambda_i I^i$$

where $A_I$ represents the intensity adjustment amount, $\lambda_i$ represents a normalizing constant for a polynomial order of i based on range, beam angle, motion information, and/or other factors, $I^i$ represents the magnitude of the focused A-line data value raised to the power of i, and m is any arbitrary value. The intensity-based adjustment $A_I$ may also depend on the coherency adjustment, $A_C$. The intensity-based adjustment may be directly proportional to the magnitude of the focused A-line value, and the adjustment amount may increase as the magnitude does. In some embodiments, intensity-based adjustment values are determined ahead of time and stored in an adjustment table 810, which may be represented in any suitable memory format including a linked list, a tree, a table such as a hash table, an associative array, a state table, a flat file, a relational database, a bitmap, and/or other memory structure. Accordingly, the determination of block 712 may include the intensity adjustment unit 808 querying the adjustment table 810 based on the magnitude of the A-line data value.

Referring to block 716, a compensation unit 812 of the focusing system 800 applies the coherency-based adjustment amount and the intensity-based adjustment amount to the focused A-line data value to obtain a clutter-filtered A-line data value. The adjustment amounts may be considered gamma adjustments, and in effect, the clutter-filtered A-line data value is a gamma corrected version of the focused A-line data value where the gamma correction amount is based on the clutter determination. In an exemplary embodiment, the compensation unit 812 includes a first digital and/or analog multiplier operable to multiply the coherency-based adjustment amount by the intensity-based adjustment amount to determine a total adjustment amount. The exemplary compensation unit 812 also includes a second digital and/or analog multiplier operable to multiply the focused A-line data value by the total adjustment amount to determine the clutter-filtered A-line data value.

Referring to block 718, an ultrasound image is obtained from a set of clutter-filtered A-line data values. By generating the image based on the clutter-filtered data, embodiments of the present disclosure can reduce or remove visual artifacts from the final image thereby providing a clearer picture of the vasculature and surrounding structures. Because this technique is part of an image forming process, it may be used in conjunction with any number of post-focusing image processing techniques to further improve image quality and alleviate clutter. For example, after the compensation unit 812 determines the clutter-filtered A-line data values, further adjustments such as image filtering, envelope filtering, log compression, gamma curve adjustment, etc. may be used to further improve image quality, sparseness, and clutter reduction.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound processing system comprising:
   an interface operable to receive A-line signal data obtained by an intravascular ultrasound (IVUS) imaging device positioned within a vessel of a patient;
   a focusing engine communicatively coupled to the interface and operable to perform a focusing process on the received A-line signal data to produce focused A-line signal data;
   a coherency unit communicatively coupled to the interface and operable to determine a measurement of phase coherency of the received A-line signal data;
   an adjustment unit communicatively coupled to the coherency unit and operable to determine an adjustment to the focused A-line signal data based on a comparison of the measurement of phase coherency to a phase coherence threshold, wherein the phase coherence threshold is associated with tissue motion information of the vessel of the patient; and
   a compensation unit communicatively coupled to the focusing engine and operable to apply the adjustment to the focused A-line signal data.

2. The ultrasound processing system of claim 1, wherein the measurement of phase coherency is an indication of artifacts within the received A-line signal data, and wherein the adjustment is determined to suppress the artifacts.

3. The ultrasound processing system of claim 1, wherein the measurement of phase coherency is based on at least one of: a sign or a phase angle of the received A-line signal data.

4. The ultrasound processing system of claim 1, wherein the measurement of phase coherency is based on a sign of the received A-line signal data, and wherein the sign represents at least one of a voltage polarity or a variance from a reference voltage.

5. The ultrasound processing system of claim 1, wherein the coherency unit is further operable to:
   assign a sign value to the received A-line signal data based on a sign of the received A-line signal data;
   add the sign value to a sign value total for a set of A-lines of an aperture corresponding to the focused A-line signal data; and
   determine the measurement of phase coherency based on the sign value total.

6. The ultrasound processing system of claim 5, wherein the coherency unit is further operable to normalize the sign value total based on a count of A-lines in the aperture, and wherein the measurement of phase coherency is further based on the normalized sign value total.

7. The ultrasound processing system of claim 1, wherein the coherency unit is further operable to:
   determine a phase angle of the received A-line signal data after a time-of-flight adjustment;
   determine, based on the phase angle, a normalized phase angle for a set of A-lines of an aperture corresponding to the focused A-line signal data; and
   determine the measurement of phase coherency based on the normalized phase angle.

8. The ultrasound processing system of claim 1, wherein the adjustment is applied based on the measurement of phase coherency exceeding the phase coherence threshold.

9. The ultrasound processing system of claim 1, wherein the adjustment unit is a first adjustment unit and wherein the adjustment is a coherency-based adjustment, the system further comprising:
   a second adjustment unit communicatively coupled to the focusing engine and operable to:
   determine a magnitude of the focused A-line signal data; and
   determine an intensity-based adjustment to the focused A-line signal data based on the magnitude of the focused A-line signal data,
   wherein the compensation unit is further operable to apply the intensity-based adjustment to the focused A-line signal data.

10. The ultrasound processing system of claim 9, wherein the intensity-based adjustment is directly proportional to the magnitude of the focused A-line signal data.

11. A method comprising:
    receiving A-line data obtained by an intravascular ultrasound (IVUS) imaging device positioned within a vessel of a patient and corresponding focused A-line data;
    determining a phase coherence metric of the A-line data across A-lines of an aperture of the focused A-line data;
    determining a clutter-reducing adjustment for the focused A-line data based on the phase coherence metric and a comparison of the phase coherence metric to a phase coherence threshold, wherein the phase coherence threshold is associated with tissue motion information of the vessel of the patient;
    applying the clutter-reducing adjustment to the focused A-line data to obtain clutter-reduced A-line data; and
    forming an ultrasound image from the clutter-reduced A-line data.

12. The method of claim 11, wherein the applying of the clutter-reducing adjustment is performed based on the phase coherence metric exceeding the phase coherence threshold.

13. The method of claim 11, wherein the phase coherence metric is based on at least one of: a sign or a phase angle of the A-line data.

14. The method of claim 13, wherein the phase coherence metric is based on the sign of the A-line data, and wherein the sign represents at least one of: a voltage polarity or a variance above or below a reference voltage.

15. The method of claim 11,
wherein the determining of the clutter-reducing adjustment includes determining a sign value total for a set of A-lines corresponding to an aperture of the focused A-line data,
wherein the sign value total includes a sign value of the received A-line data, and
wherein the phase coherence metric is based on the sign value total.

16. The method of claim 15, wherein the determining of the clutter-reducing adjustment further includes normalizing the sign value total based on a count of A-lines of the aperture, and wherein the phase coherence metric is further based on the normalized sign value total.

17. The method of claim 11,
wherein the determining of the clutter-reducing adjustment includes determining a phase angle sum including a phase angle of the received A-line data, and wherein the phase coherence metric is based on the phase angle sum.

18. The method of claim 11 further comprising:
determining a magnitude of the focused A-line data, and
determining the clutter-reducing adjustment for the focused A-line data further based on the magnitude.

19. The method of claim 18, wherein the clutter-reducing adjustment is determined to be directly proportional to the magnitude.

20. A method of clutter reduction, the method comprising:
receiving ultrasound data obtained by an intravascular ultrasound (IVUS) imaging device positioned within a vessel of a patient;
determining an indication of artifacts in the ultrasound data based on phase coherence of the ultrasound data;
performing a focusing process on the ultrasound data to produce focused ultrasound data;
determining whether to apply a gamma correction to the focused ultrasound data based on a comparison of the phase coherence-based indication to a phase coherence threshold,
wherein the phase coherence threshold is associated with tissue motion information of the vessel of the patient; and
applying, in response to the determining, the gamma correction to the focused ultrasound data based on the indication of artifacts to suppress an effect of the artifacts.

21. The method of claim 20, wherein the applying of the gamma correction is based on a measure of the phase coherence of the ultrasound data exceeding the phase coherence threshold.

22. The method of claim 20 further comprising: determining the phase coherence of the ultrasound data based on at least one of: a sign or a post-time-of-flight adjusted phase angle of the ultrasound data.

23. The method of claim 20 further comprising: determining the phase coherence of the ultrasound data by accumulating a sign value total of the ultrasound data and normalizing the sign value total based on a number of A-lines in an aperture of the focused ultrasound data, wherein the phase coherence is determined based on the normalized sign value total.

24. The method of claim 20 further comprising determining the phase coherence of the ultrasound data by accumulating a phase angle total of the ultrasound data and normalizing the phase angle total based on a number of A-lines in an aperture of the focused ultrasound data, wherein the phase coherence is determined based on the normalized phase angle total.

25. The method of claim 20 further comprising determining a magnitude of the focused ultrasound data, wherein the gamma correction is based on the magnitude of the focused ultrasound data.

* * * * *